(12) United States Patent
Katahira et al.

(10) Patent No.: US 6,229,912 B1
(45) Date of Patent: May 8, 2001

(54) PARTICLE IMAGE ANALYZING APPARATUS

(75) Inventors: Hatsue Katahira; Kazuhiro Sano, both of Ibaraki-ken; Hideki Asai, Mito; Norio Oowada, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 08/943,468

(22) Filed: Oct. 3, 1997

Related U.S. Application Data (63) Continuation of application No. 08/358,027, filed on Dec. 15, 1994, now abandoned.

(30) Foreign Application Priority Data

Dec. 22, 1993 (JP) .................................................. 5/323955

(51) Int. Cl.[7] .................................................. G06K 9/00
(52) U.S. Cl. ........................ 382/133; 382/224; 422/68.1; 702/21
(58) Field of Search ................................. 382/364, 395, 382/756, 128–134, 170, 194, 224, 190, 192; 204/543; 210/645; 250/461.2; 365/167; 436/74, 43; 356/39; 73/61.71; 702/21; 600/300; 435/4, 7.23; 422/68.1

(56) References Cited

U.S. PATENT DOCUMENTS

| | | | |
|---|---|---|---|
| 4,199,748 | * 4/1980 | Bacus | 382/197 |
| 4,393,466 | 7/1983 | Deindoerfer et al. | 364/415 |
| 4,412,285 | * 10/1983 | Neches et al. | 395/673 |
| 5,212,784 | * 5/1993 | Sparks | 395/575 |
| 5,257,182 | * 10/1993 | Luck et al. | 364/413.1 |
| 5,276,865 | * 1/1994 | Thorpe | 393/575 |
| 5,488,469 | * 1/1996 | Yamamoto et al. | 356/72 |
| 5,548,395 | * 8/1996 | Kosaka | 356/73 |

FOREIGN PATENT DOCUMENTS

| | | |
|---|---|---|
| 571053 | 11/1986 | (EP) . |
| 336608 | 3/1989 | (EP) . |
| 543514 | 10/1992 | (EP) . |
| 50-68330 | 7/1975 | (JP) . |
| 58-76740 | 9/1983 | (JP) . |
| WO-A-9213308 | 1/1992 | (WO) . |
| WO-A-9316436 | 2/1993 | (WO) . |

* cited by examiner

Primary Examiner—Jay Patel
(74) Attorney, Agent, or Firm—Mattingly, Stanger & Malur, P.C.

(57) ABSTRACT

A particle image analyzing apparatus of high classifying accuracy and high efficiency in which a criterion for determining whether fine classification is required or not can be set for every facility such as hospital, or the like. A rough classification unit executes rough classification of particles and supplies results of the rough classification to a fine classification necessity determination unit. The necessity determination unit compares the results of the rough classification with reference values stored in a reference value storage unit and determines from the comparison whether every sample is normal or abnormal to thereby determine whether fine classification is required or not. The reference values stored in the storage unit can be changed in accordance with the subject of examination through an input/output control unit from a keyboard. When the determination unit makes a decision that fine classification is required, the determination unit gives an instruction to an image processing control circuit to execute fine classification. Characteristic parameters for fine classification are supplied to a fine classification unit on the basis of the control instruction of the control circuit. Then, fine classification is executed, so that results of the fine classification are supplied to the determination unit.

5 Claims, 9 Drawing Sheets

FIG.4

SCREEN FOR SETTING REFERENCE VALUES FOR CHECKING ABNORMAL SAMPLES

REFERENCE VALUE

1 WHITE CORPSCLES             2   OR MORE/FIELD ~60
2 RED CORPSCLES               3   OR MORE/FIELD ~60
3 SQUAMOUS EPITHELIAL CELLS   1   OR MORE/FIELD ~60
4 TRANSITIONAL EPITHELIAL CELLS  1  OR MORE/FIELD ~60
5 OTHER EPITHELIAL CELLS      1   OR MORE/FIELD ~60
6 VITEROUS HYALINE CASTS     10   OR MORE/FIELD ~60
7 OTHER HYALINE CASTS         1   OR MORE/FIELD ~60
8 BACTERIA                    1   OR MORE/FIELD ~60

PARTICLE IMAGE ANALYZING APPARATUS

This application is a continuation of application Ser. No. 08/358,027, filed Dec. 15, 1994, now abandoned.

BACKGROUND OF THE INVENTION

The present invention relates to a particle image analyzing apparatus in which images of particles suspended in a liquid sample are picked up in order to analyze the particles and, more particularly, relates to a particle image analyzing apparatus suitable for analysis of cells or particles contained in blood or urine.

For example, cells or particles contained in blood or urine have been heretofore analyzed by preparing a specific sample on a microscope slide and observing it through a microscope. As for urine, because the concentration of particles in urine is low, a sample of urine is centrifugally condensed by a centrifugal separator before the sample is observed.

There is an apparatus for automatizing these observing and examining operations. In the automatizing apparatus, a microscope slide is smeared with a sample of blood or the like and then set in a microscope. Then, the slide on the stage of the microscope is stopped at a suitable location where particles are present, through automatic scanning. Next, still images of the particles are picked up, so that the classification of the particles in the sample, or the like, is performed by means of characteristic extraction and pattern recognition based on image processing techniques.

An example of the aforementioned automatizing apparatus using microscope slides is an apparatus for automatically reexamining slide samples, described in JP-A 50-68330. In the automatic reexamination apparatus, various kinds of blood corpuscles or the like on microscope slides are analyzed automatically and where the results of automatic analysis are inconclusive, samples are moved to a reexamination position where the samples are reexamined directly by a surveyor or the like.

In the aforementioned automatizing apparatus, however, a long time is required for smearing a microscope slide with a sample. Moreover, extra work is required for detecting particles while moving the stage of a microscope mechanically and for moving the particles to a suitable image pickup zone in the visual field of the microscope. Accordingly, the aforementioned automatizing apparatus requires a long period of time to analyze each sample and comprises complex mechanical construction.

On the other hand, there is a particle analyzing method using a flow sight meter in which particles to be examined are analyzed optically while the particles are suspended in a fluid sample and are moved in a flow chamber continuously without smearing a specific sample over a microscope slide (for example, a method of analyzing particles of a dilute fluid sample as described in JP-A 58-76740). The particle analyzing method using a flow sight meter serves to observe the intensity of fluorescence and the intensity of scattered light from respective particles in a fluid sample and has a processing capacity of 1000 per second.

There is also an analyzing apparatus in which: still images of particles contained in a fluid sample are picked up by means of a flash lamp while the fluid sample is poured into a wide image pickup zone through a specific-form flow path; and the particles are analyzed by using the images thus picked up. In the analyzing apparatus, the flash lamp serving as a pulse light source emits light periodically in synchronism with the operation of a charge coupled device (CCD) camera and images of sample particles are enlarged by a microscope, so that the enlarged images are projected onto the CCD camera. The light-emitting time of the pulse light source is short, so that still images can be picked up even though the fluid sample containing particles is poured continuously.

SUMMARY OF THE INVENTION

In general clinical examinations, analysis of a fluid sample is roughly separated into the following two processes.

The first process is a screening process which aims at discriminating samples suspected of being abnormal samples from a large number of samples obtained from general persons.

The second process is a disease defining process aimed at classifying in greater detail samples suspected of being abnormal samples defining diseases on the basis of characteristics of individual components or the like.

In a particle image analyzing apparatus in which only rough classification is carried out for the purpose of screening as the first process, a large number of samples can be processed. Samples suspected of being abnormal samples, however, require reexamination. Therefore, microscope slides smeared with samples to be reexamined must be formed so as to be observed under a microscope. Thus, where reexamination is necessary, a long period of time is required to define the disease and a greater quantity of sample is required to perform both examinations. It is undesirable that a person whose disease must be defined rapidly to start medical treatment be subjected to two examinations.

On the other hand, in a particle image analyzing apparatus in which only fine classification is carried out for the purpose of defining diseases as the second process, all samples must be subjected to extraction and identification of a large number of characteristic parameters, so that such a large number of samples cannot be processed in a short time.

To this end, the following method may be considered. Characteristic parameters for each sample are extracted and stored in advance. Then, rough classification, equivalent to the first process, is executed to determine whether the sample should be subjected to fine classification. Then, the sample requiring fine classification is finely classified automatically by using the stored characteristic parameters. By this method, analysis high in classifying accuracy and high in efficiency can be performed.

Further, it is sometimes necessary to vary the criterion upon which the decision to perform fine classification is based. That is, for example in a hospital, the criterion for determination with respect to inpatients may differ from the criterion for determination with respect to outpatients. Further, the criterion for determination may vary between males and females. Further, there is a case where the criterion of determination is different between male and female persons. Further, in a special hospital or the like, the criterion for determination may vary for every hospital because the influence of medicines to be administered must be considered.

An object of the present invention is to provide a particle image analyzing apparatus of high classifying accuracy and high efficiency, in which the criterion for determining whether fine classification is required can be set for every facility, such as hospitals or the like.

To achieve the foregoing object, the present invention is configured as follows.

According to an aspect of the present invention, there is provided a particle image analyzing apparatus including an image picking-up unit for picking-up images of particles contained in a fluid sample, and an image analyzing unit for analyzing the images of the particles picked up by the image picking-up unit, the apparatus further including: a reference value input unit for inputting a reference value for determining whether the fluid sample is abnormal or normal; a reference value storage unit for storing the reference value given by the input unit so that the stored reference value can be changed by the input unit; a rough classification unit for discriminating the fluid sample whether it is abnormal or normal by classifying the images of the particles on the basis of the reference value stored in the storage unit; and a fine classification unit for defining the kind of abnormality by classifying the particle images of the fluid sample when the rough classification unit makes a decision that the fluid sample is abnormal.

According to another aspect of the present invention, there is provided a particle image analyzing apparatus including an image picking-up unit for picking-up images of particles contained in a fluid sample, and an image analyzing unit for analyzing the images of the particles picked up by the image picking-up unit, the apparatus further including: a reference value input unit for inputting a reference value for determining whether the fluid sample is abnormal or normal; a reference value storage unit for storing the reference value given by the input unit so that the stored reference value can be changed by the input unit; a rough classification unit for extracting primary characteristic from the images of the particles picked up by the image picking-up unit and determining whether the fluid sample is normal by determining the images of the particles on the basis of the reference value stored in the storage unit; and a fine classification unit for defining the kind of abnormality by extracting secondary characteristic larger in the quantity of information than the primary information from the images of the particle images of the fluid sample when the rough classification unit cannot make a decision that the fluid sample is normal, by discriminating the fluid sample whether it is abnormal or normal on the basis of the reference value stored in the storage unit and by classifying the images of the particles of the fluid sample on the basis of the primary and secondary characteristics when a decision is made that the fluid sample is abnormal.

Preferably, the aforementioned particle image analyzing apparatus further comprises a display unit in which the reference value set for every kind of the particles can be displayed on the basis of the input from the reference value input unit.

Preferably, in the aforementioned particle image analyzing apparatus, the fluid sample is urine or blood.

Preferably, the aforementioned particle image analyzing apparatus further comprises a flow chamber through which the fluid sample containing particles passes so that the image picking-up unit picks up images of the particles in the flow chamber.

Preferably, the aforementioned particle image analyzing apparatus further comprises a spare time determination unit in which: an operating point of time when an analyzing operation as described above is executed is stored for predetermined days; a plurality of spare times free from execution of the analyzing operation are calculated on the basis of the stored operating point of time and stored; and particle image data obtained by image picking-up is transferred to an external storage unit in a spare time selected from the plurality of spare times thus calculated.

Preferably, in the aforementioned particle image analyzing apparatus, if at least the image analyzing unit is operating in the selected spare time, the spare time determination unit selects another spare time and transfers the particle image data to the external storage unit.

For example, reference values required for every hospital are inputted by an operator using the reference value input unit. The thus inputted reference values are stored in the reference value storage unit. The reference values stored in the storage unit can be set again for every kind of the fluid sample through the reference value input unit. The rough classification unit determines from the picked-up images of particles and on the basis of the stored reference values whether the fluid sample is abnormal or normal. The images of particles in the fluid sample determined as being abnormal by the rough classification unit are finely classified by the fine classification unit to define the kind of abnormality. In this manner, the criterion for determining whether fine classification is required or not can be set for every facility such as hospital, or the like, so that a particle image analyzing apparatus high in classifying accuracy and high in efficiency can be provided.

Further, time zones free from the analyzing operation of the particle image analyzing apparatus are calculated by a spare time calculation unit, so that the picked-up images of particles are transferred to the external storage unit in the spare time zones thus calculated. In this manner, a particle image analyzing apparatus in which not only high classifying accuracy and high efficiency can be obtained but also information of samples to be examined can be transferred without influence on the analyzing operation.

DETAILED DESCRIPTION OF THE PREFERRED EMBODIMENTS

Figure 1:
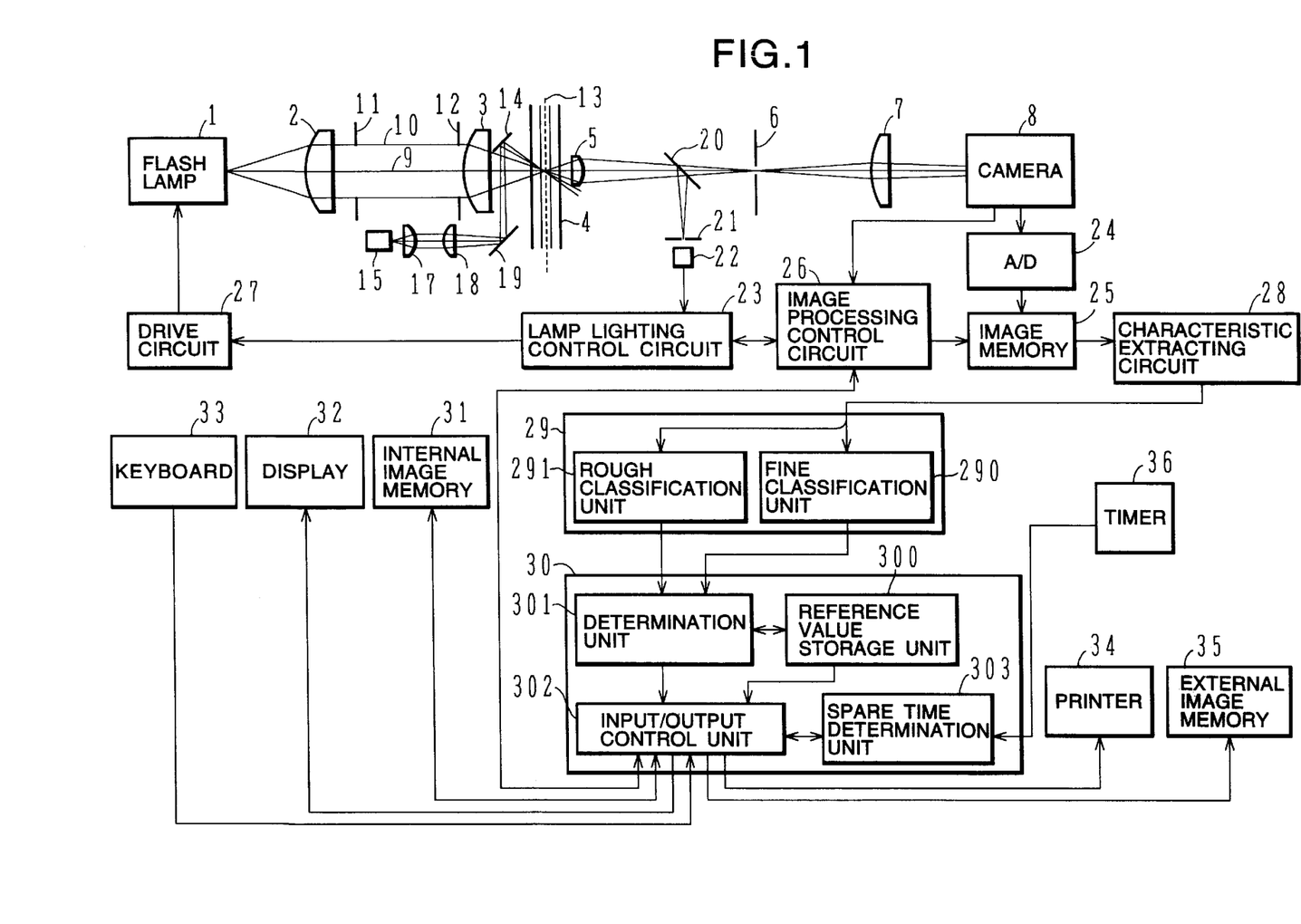
FIG. 1 is a schematic structural diagram of an apparatus as a first embodiment of the present invention.

FIG. 1 is a schematic structural diagram of a flow type particle image analyzing apparatus as a first embodiment of the present invention.

In FIG. 1, light emitted from a flash lamp 1 as a microscopic light source advances on a microscopic light axis 9, passes through a field lens 2 and a field diaphragm 11 to form luminous flux 10, passes through an aperture diaphragm 12 and a condenser lens 3 and converges on a flow 13 of a sample such as urine, or the like, in a flow chamber 4.

A particle image of the sample flow 13 is formed at an image-forming position 6 by a microscopic objective lens 5. The image at the image-forming position 6 is projected onto an image pickup surface of a TV camera 8 by a projection by a projection lens 7 and photoelectrically converted by the TV camera 8. A CCD type TV camera with a small after image is generally used as the TV camera.

The timing of emitting light from the flash lamp 1 is controlled on the basis of a signal detected by a particle detecting system. That is, when a lighting signal from a flash lamp lighting control circuit 23 is supplied to a lamp drive circuit 27, the flash lamp 1 is lighted by the drive circuit 27. The lighting control circuit 23 generates a lighting signal on the basis of light generated by a semiconductor laser generator 15.

The semiconductor laser generator 15 is always switched on, so that light generated by the semiconductor laser generator 15 is collimated into parallel luminous flux by a collimator lens 17 and focused unidirectionally by a cylindrical lens 18. Then, the light from the cylindrical lens 18 is radiated onto the sample flow 13 in the flow chamber 4 through a reflector 19 and a micro-reflector 14. When the laser luminous flux is radiated onto particles in the suspension to be measured, the laser light is scattered. The scattered light is focused by the microscopic objective lens 5 for picking-up images of the particles and then reflected by a beam splitter 20. The light from the beam splitter 20 is supplied to a diaphragm 21, so that the light is supplied to a photodetector 22 while the observation area on the sample flow is limited. The light supplied to the photodetector 22 is converted into an electric signal to form a particle detection signal. The particle detection signal is supplied to a flash lamp lighting control circuit 23.

As described above, the semiconductor laser generator 15 is always switched on, so that whether particles in the sample pass through the detection zone or not is always observed. When the particle detection signal based on scattering of light caused by the passage of particles through the detection zone is not smaller than a predetermined value, the flash lamp lighting control circuit 23 determines the particles as a subject of image processing and controls the lamp drive circuit 27 to switch on the flash lamp 1 when the particles reach a predetermined position in the image pickup zone of the TV camera 8.

Because the light-emitting time of the flash lamp 1 is set to be so short that the quantity of the movement of particles in the sample flow for the light-emitting time can be neglected, the video output signal of the TV camera 8 can form the image of the particles in the sample flow as a still image when the flash lamp 1 is lighted. Writing of image data into an image memory 25 and image processing after that are controlled by an image processing control circuit 26.

That is, the video output signal of the TV camera 8 is supplied to the image memory 25 through an A/D converter 24. From the image stored in the image memory 25, primary parameters such as shape, color, size, etc. of the particles are extracted by a characteristic extracting circuit 28. The image processing control circuit 26 inputs these primary parameters and secondary parameters created by arithmetic operations using combinations of these primary parameters into an identifying circuit 29.

Then, a rough classification unit 291 of the identifying circuit 29 roughly classifies the particles on the basis of the primary and secondary parameters thus extracted. A result of the rough classification executed by the rough classification unit 291 is supplied to a fine classification necessity determination unit 301 of a central control unit 30 for determining whether fine classification is required. The fine classification necessity determination unit 301 compares the result of the rough classification with the reference value stored in the reference value storage unit 300 and determines from analysis conditions whether the sample is normal or abnormal to thereby determine whether fine classification is required or not. The reference value stored in the reference value storage unit 300 is set through an input/output control unit 302 from a keyboard 33, so that the reference value to be stored in the reference value storage unit 300 can be changed in accordance with the change of the subject of examination, or the like.

When the fine classification necessity determination unit 301 makes a decision that fine classification is required, an instruction is given to the image processing control circuit 26 through the input/output control unit 302 to execute fine classification. On the basis of a control instruction signal from the image processing control circuit 26, characteristic parameters for fine classification are supplied to a fine classification unit 290 of the identifying circuit 29 from the characteristic extracting circuit 28.

Then, fine classification (for example, fine classification based on the neural network identifying theory to define a disease) is executed in the fine classification unit 290. A result of the fine classification as a final result is supplied to the determination unit 301 of the central control unit 30. The determination unit 301 stores the particle image in an internal image memory 31 and displays the classification result on a display unit 32 or through a printer 34 in accordance with an instruction from the keyboard 33 or the like.

Figure 2:
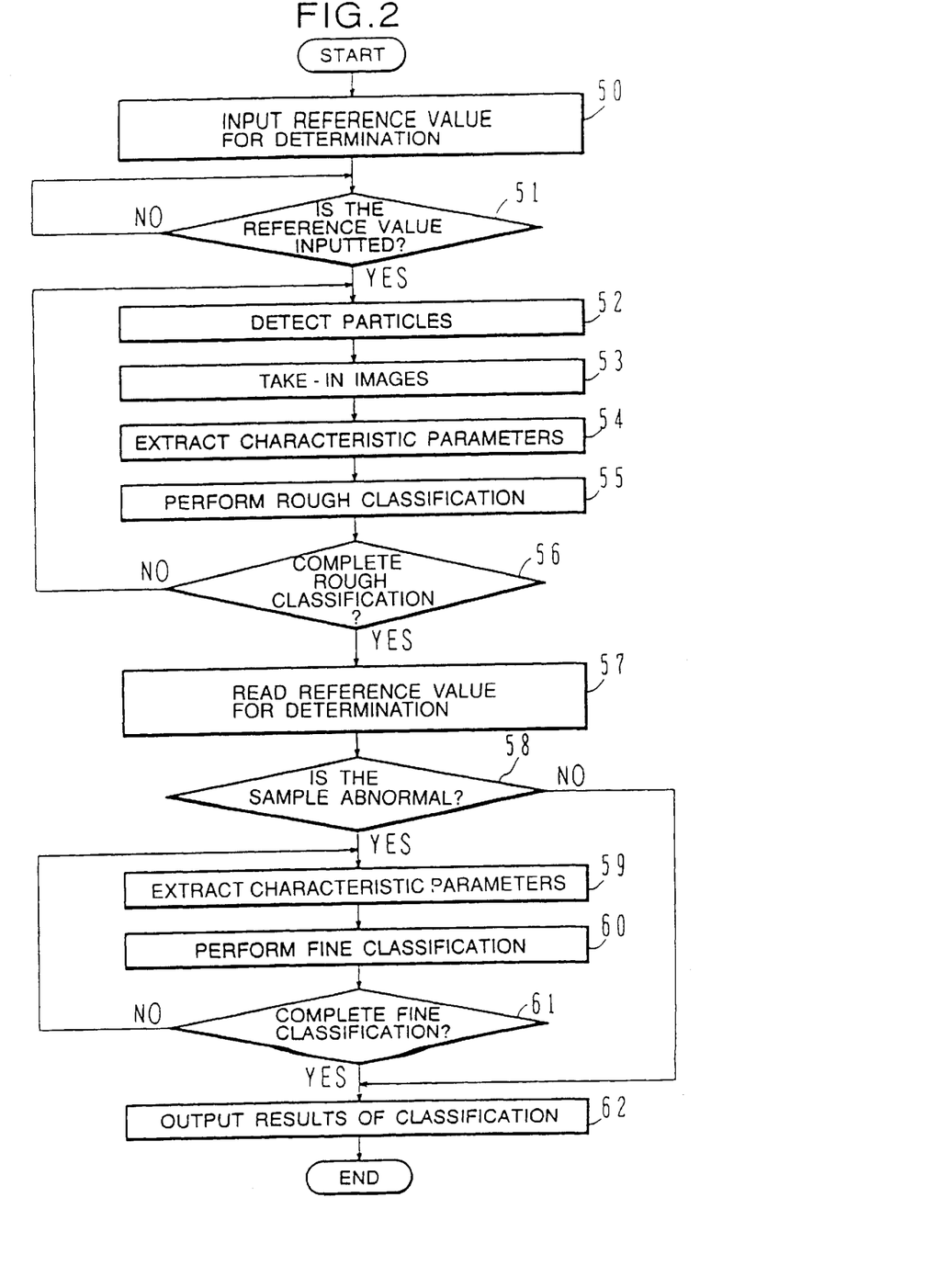
FIG. 2 is a flow chart showing the operation of the apparatus depicted in FIG. 1.

FIG. 2 is a flow chart used for explaining the operation of the embodiment shown in FIG. 1.

In step 50 in FIG. 2, a reference value for determining whether fine classification is required or not is inputted into the reference value storage unit 300 through the input/output control unit 302 from the keyboard 33. In step 51, a determination is made as to whether the inputting of the reference value is completed or not.

Figure 3:
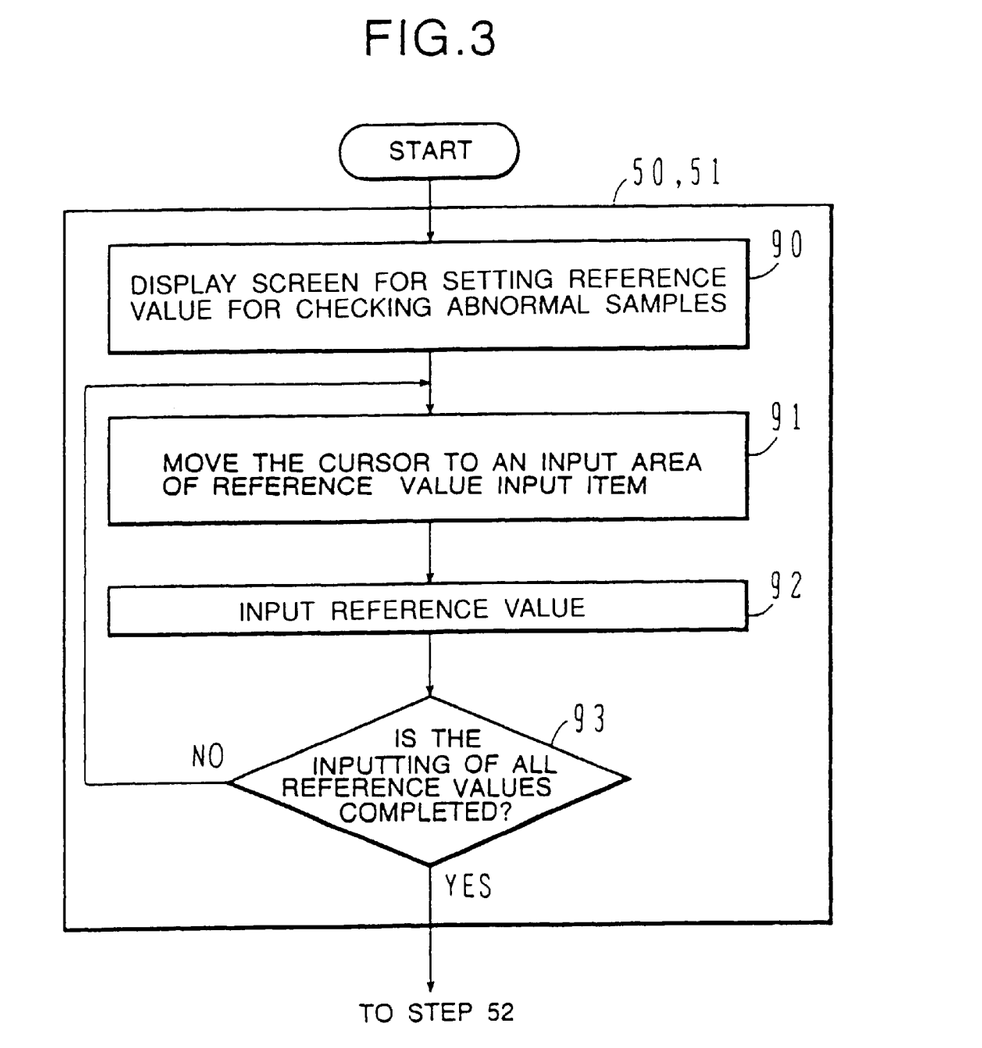
FIG. 3 is a flow chart showing a routine of setting reference values for determining abnormal samples.

FIG. 3 is a detailed flow chart of the reference value input steps 50 and 51. In step 90 in FIG. 3, a screen for setting a reference value for checking abnormal samples is given on the display unit 32. Then, in step 91, the keyboard 33 is operated to move the cursor to an input area of an item for inputting the reference value. Then, in step 92, the keyboard 33 is operated to input the reference value. Then, in step 93, a determination is made as to whether the inputting of reference values for all items is completed or not. When it is determined that the inputting of all reference values is not completed, the process returns to the step 91. When it is determined that the inputting of reference values for all items is completed in the step 93, the process proceeds to step 52.

Figure 4:
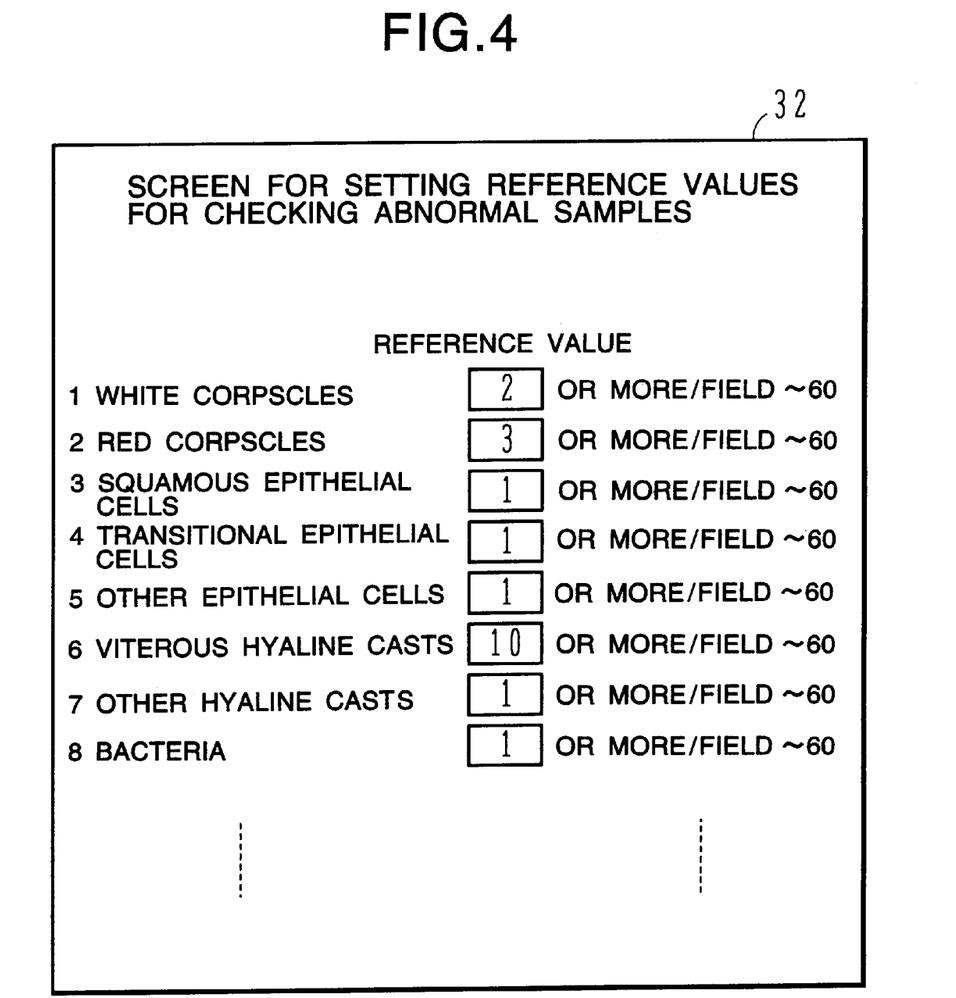
FIG. 4 is a view showing an example of a screen for setting the reference values for determining abnormal samples.

FIG. 4 shows an example of the display screen on the display unit 32 in the reference value input steps 50 and 51.

In FIG. 4, when the number of white corpuscles is not smaller than 2 in one field, a decision is made that the sample is abnormal and requires fine classification. Similarly, when the number of red corpuscles is not smaller than 3, when the number of squamous epithelial cells is not smaller than 1, when the number of transitional epithelial cells is not smaller than 1, when the number of other epithelial cells is not smaller than 1, when the number of vitreous hyaline casts is not smaller than 10, when the number of other casts is not smaller than 1 or when the number of bacteria is not smaller than 1, a decision is made that the sample is abnormal and requires fine classification.

The reference values stored in the reference value storage unit 300 can be changed in accordance with the subject to be examined.

When the process proceeds to the step 52 from the step 51 of FIG. 2, detection of particles is executed. After the detection of the particles, in the step 53, images of the particles are fetched in the image memory 25. Then, in step 54, characteristic parameters are extracted from the images of the particles by the characteristic extracting circuit 28. Then, in step 55, rough classification is executed by the rough classification unit 291. Next, in step 56, a determination is made as to whether rough classification is completed or not. When it is determined that rough classification is not completed, the process returns to the step 52. When it is determined that rough classification is completed in the step 56, the process proceeds to step 57 in which reference values stored in the reference value storage unit 300 are read.

Then, in the step 58, a determination is made from results of the rough classification as to whether the sample is abnormal or not. When it is determined that the sample is not abnormal, the process proceeds to step 62 in which the results of the classification are displayed on the display unit 32 or through the printer 34. When it is determined that the sample is abnormal in the step 58, the process proceeds to step 59 in which characteristic parameters for fine classification are extracted. Then, in step 60, fine classification is executed to define the kind of abnormality. Then, in step 61, a determination is made as to whether fine classification is completed or not. When it is determined that fine classification is not completed, the process returns to the step 59. When it is determined that fine classification is completed in the step 61, the process proceeds to the step 62 in which results of the classification are displayed.

As described above, in the first embodiment of the present invention, reference values for determining whether the roughly classified sample requires fine classification or not can be set for every sample or every facility. Accordingly, a particle image analyzing apparatus high in classifying accuracy and high in efficiency can be provided.

In clinical examinations, in addition to being finely analyzed, recognized abnormal samples are further analyzed to determine the shapes of individual particles, or the like. Further, some abnormal samples may require observation with the passage of time. Further, in the case of rare or valuable samples, it is necessary to preserve image data and analysis result data thereof for a long term. Long-term preservation of analysis result data in the particle image analyzing apparatus requires an undesirable increase in storage capacity. It is therefore necessary to transfer data to be preserved to an external storage unit from the particle image analyzing apparatus. When data is to be transferred to such an external storage unit, it is however necessary to interrupt the analyzing operation of the particle image analyzing apparatus. Accordingly, the data transferring operation can be carried out in a spare time when the analyzing operation of the particle image analyzing apparatus is not executed. The spare time, however, varies in accordance with facilities in which this type of particle image analyzing apparatus is used.

In the particle image analyzing apparatus according to the first embodiment of the present invention, therefore, the aforementioned spare time is detected automatically so that image data can be transferred to the external storage unit in the thus detected spare time automatically.

Figure 5:
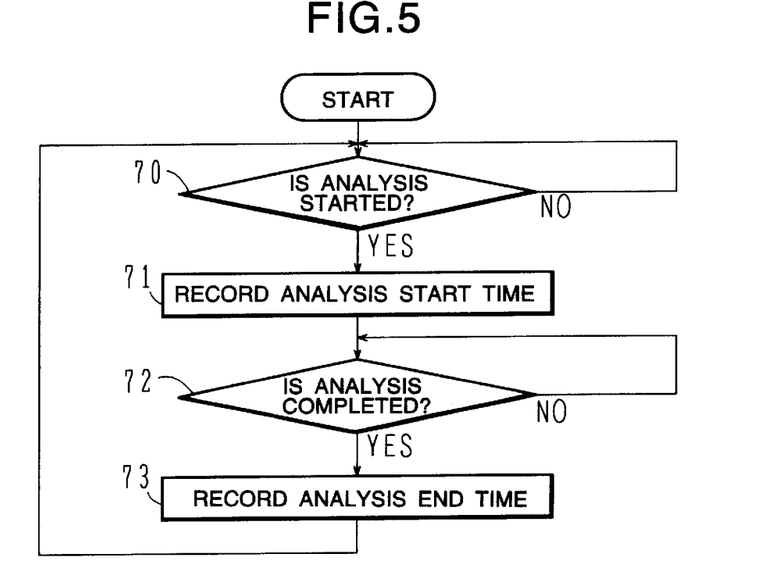
FIG. 5 is a flow chart showing an operation for storing a time zone in which an analyzing operation is carried out.
Figure 6:
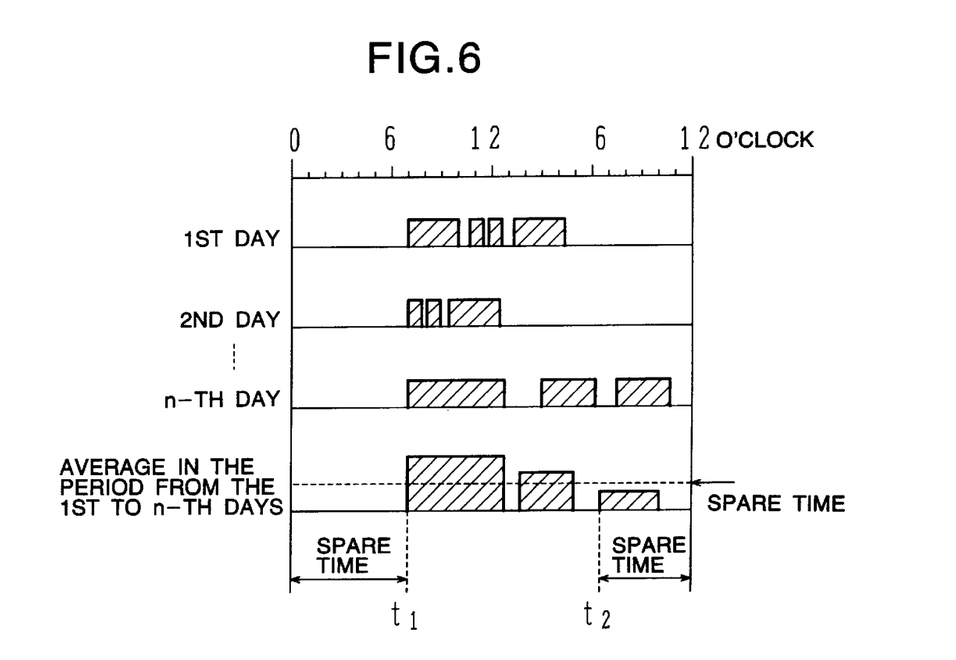
FIG. 6 is a view for explaining detection of spare time.

FIG. 5 is a flow chart showing a routine for storing an analysis start point of time and an analysis end point of time. FIG. 6 is a view for explaining the detection of the spare time. Incidentally, the detection of the spare time is executed by a spare time determination unit 303 in the embodiment shown in FIG. 1.

In step 70 in FIG. 5, the spare time determination unit 303 determines from the control state of the input/output control unit 302 whether analysis has been started or not. When it is determined that analysis has been started, in step 71, a time signal from a timer 36 is fetched so that the analysis start point of time is stored. Then, in step 72, a determination is made as to whether the analysis is completed or not. When the analysis is completed, in step 73, the spare time determination unit 303 fetches a time signal from the timer 36 so that the analysis end point of time is stored. Then the process returns to the step 70. Thus, analysis start points of time and analysis end points of time for a predetermined number n of days are detected and stored. Periods of analyzing operations of the particle image analyzing apparatus are averaged by each point of time so that time zones shorter than a predetermined reference value and longer than the time required for writing image data, that is, longer than the time required for transferring image data are set as spare times of the apparatus. The thus set spare times form time zones for the data transferring operation.

That is, for example in FIG., 6, the particle image analyzing apparatus is used for a period of from six o'clock to ten o'clock, for a period of from half past ten to half past eleven, for a period of from twelve o'clock to one o'clock and for a period of from half past one to half past four on the first day. In this manner, periods of use of the apparatus on the second, third, . . . , n-th day are stored. All the periods of use from the first day to the n-th day are averaged, so that the period of from zero o'clock to time point $t_1$ and the period of from time point $t_2$ to twelve o'clock, which periods are time zones shorter than a predetermined reference value for spare time and longer than the time required for writing image data, are determined as spare time zones. The spare time determination unit 303 supplies an instruction signal to the input/output control unit 302 to transfer image data to the external image memory 35 in the spare time zones.

Figure 7:
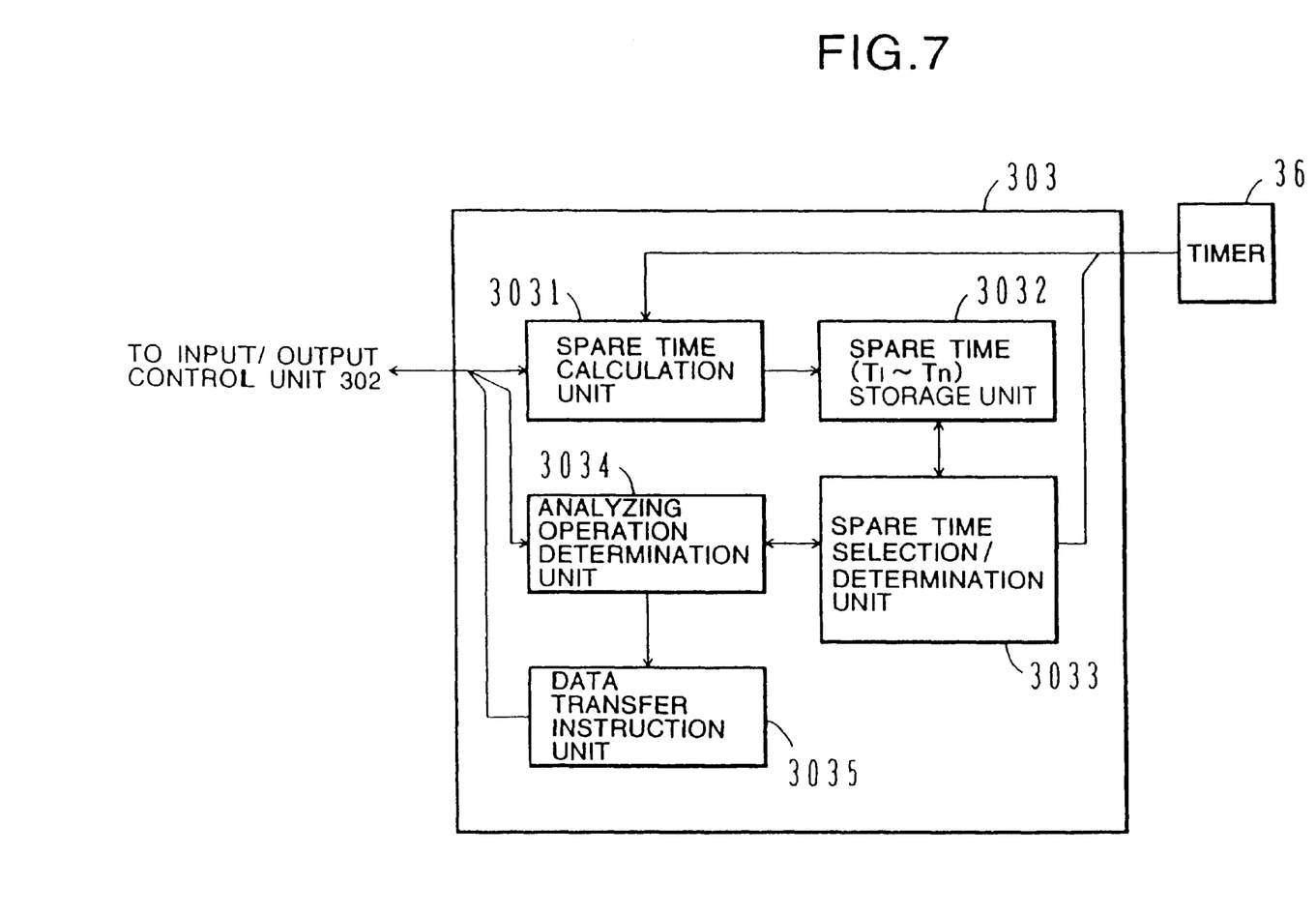
FIG. 7 is a block diagram showing the internal structure of a spare time determination unit.

FIG. 7 is a block diagram showing the internal structure of the spare time determination unit 303. In FIG. 7, a spare time calculation unit 3031 fetches a time signal from the timer 36, detects analysis start points of time and analysis end points of time from the signal input/output condition of the input/output control unit 302 and calculates a plurality of spare times $T_1$ to $T_n$. The spare time calculation unit 3031 stores the thus calculated spare times $T_1$ to $T_n$ in a spare time storage unit 3032.

A spare time selection/determination unit 3033 fetches a time signal from the timer 36, selects a spare time nearest to the present point of time from the spare times $T_1$ to $T_n$ stored in the spare time storage unit 3032 and determines whether the selected spare time has come or not. When the selected spare time has come, the spare time selection/determination unit 3033 supplies an instruction signal to an analyzing operation determination unit 3034 in order to notify the determination unit 304 that the spare time has come.

Upon reception of the instruction signal from the spare time selection/determination unit 3033, the analyzing operation determination unit 3034 determines from the signal input/output condition of the input/output control unit 302 whether the apparatus is in analyzing operation or not. If the apparatus is not in analyzing operation, the analyzing operation determination unit 3034 supplies an operating instruction signal to a data transfer instruction unit 3035 80. Upon reception of the operating instruction signal from the analyzing operation determination unit 3034, the data transfer instruction unit 3035 supplies an instruction to the input/output control unit 302 so that transferring of data stored in the automatic analyzing apparatus to the external image memory 35 is started.

Figure 8:
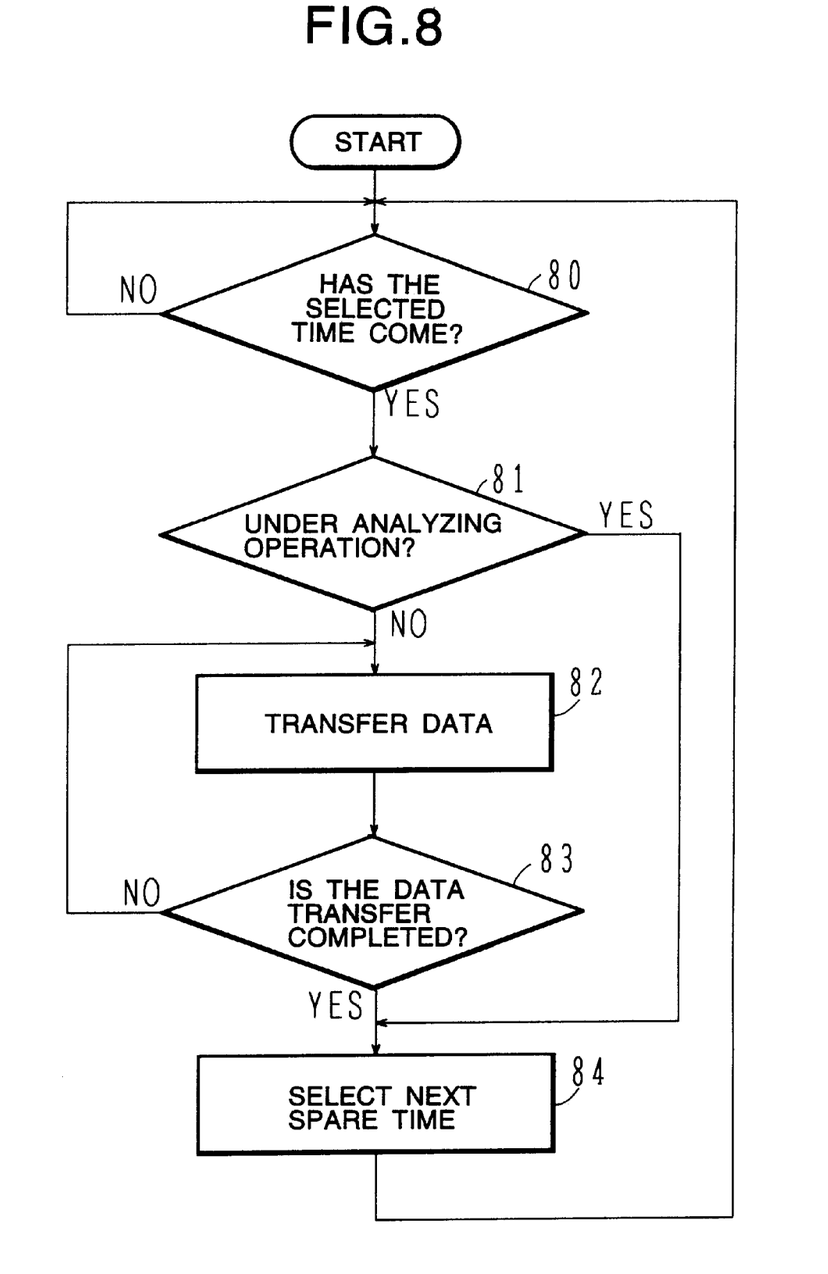
FIG. 8 is a flow chart showing the operation of the spare time determination unit.

FIG. 8 is a flow chart showing the operation of the aforementioned spare time determination unit 303. In step 80 in FIG. 8, the spare time selection/determination unit 3033 determines whether the selected spare time has come or not. When it is determined that the spare time has come, the process proceeds to step 81 in which the analyzing operation determination unit 3034 determines whether the automatic analyzing apparatus is in analyzing operation or not. When it is determined that the automatic analyzing apparatus is in analyzing operation, the analyzing operation determination unit 3034 transmits the fact that the apparatus is in analyzing operation, to the spare time selection/determination unit 3033. Then, the process proceeds to step 84. In the step 84, the spare time selection/determination section 3033 selects the next spare time. Then the process returns to the step 80.

When it is determined that the automatic analyzing apparatus is not in analyzing operation in the step 81, the process proceeds to step 82. In the step 82, the data transfer instruction unit 3035 supplies a data transfer starting instruction to the input/output control unit 302. Then, in step 83, the data transfer instruction unit 3035 determines whether the data transfer is completed or not. When it is determined that the data transfer is not completed, the process returns to the step 82. When it is determined that the data transfer is completed, the process proceeds to step 84. In the step 84, the next spare time is selected in the manner as described above and then the process returns to the step 80.

As described above, in the first embodiment of the present invention, time zones free from the analyzing operation of the automatic analyzing apparatus are retrieved automatically so that image data obtained by image picking-up can be automatically transferred to the external storage unit in the spare time zones. Accordingly, transferring of image data obtained by image picking-up can be executed securely regardless of difference in spare time between respective facilities.

Incidentally, during the transferring of data, the fact that data transfer is currently in operation, data transfer end schedule time, and so on, can be displayed on the display unit 32.

Further, when a sample must be immediately analyzed while the apparatus is in the process of transferring data, the data transfer may be interrupted by operating the keyboard, or the like, so that not-transferred data will be transferred in the next spare time automatically.

Figure 9:
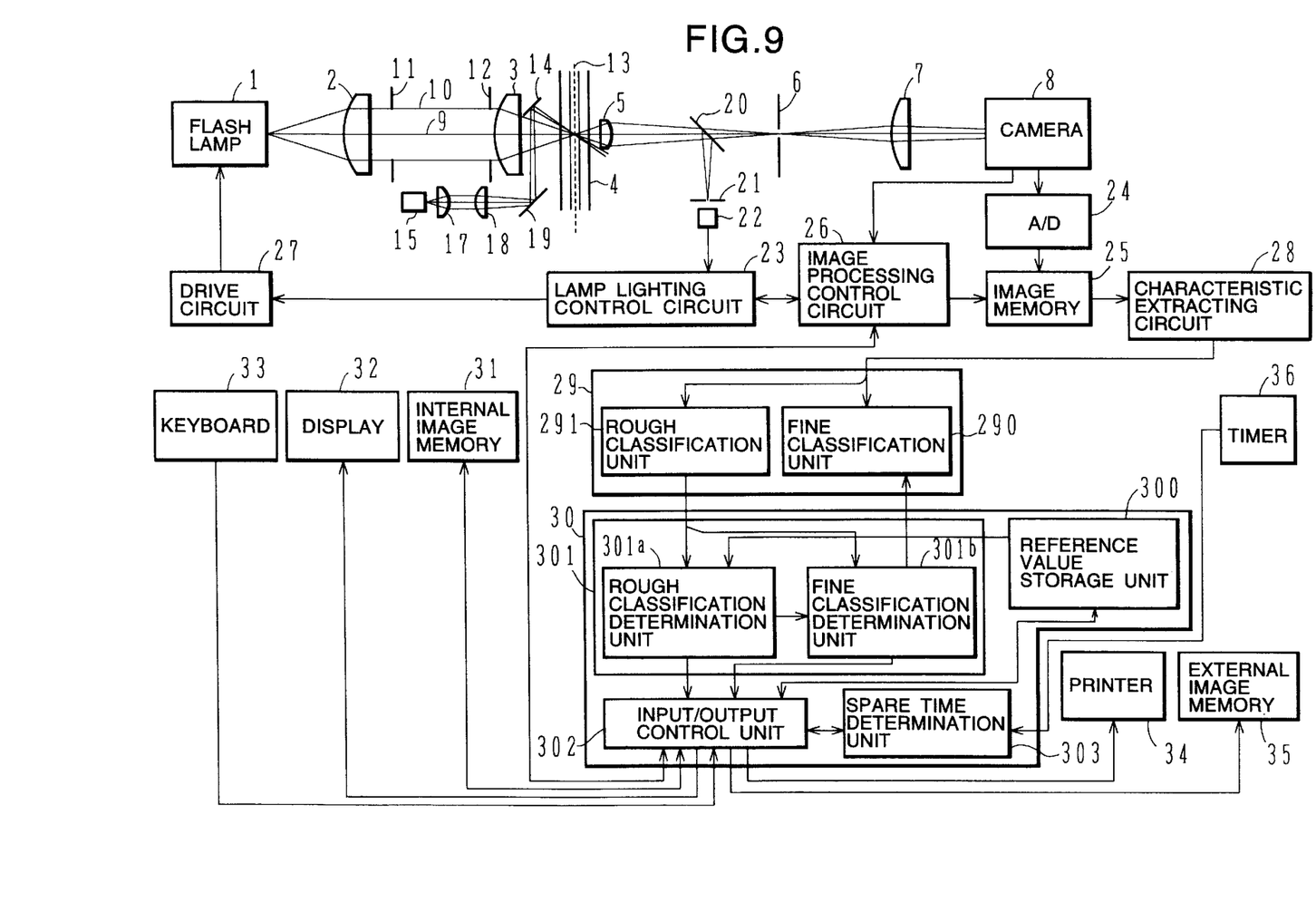
FIG. 9 is a schematic structural diagram of an apparatus as a second embodiment of the present invention.
Figure 10:
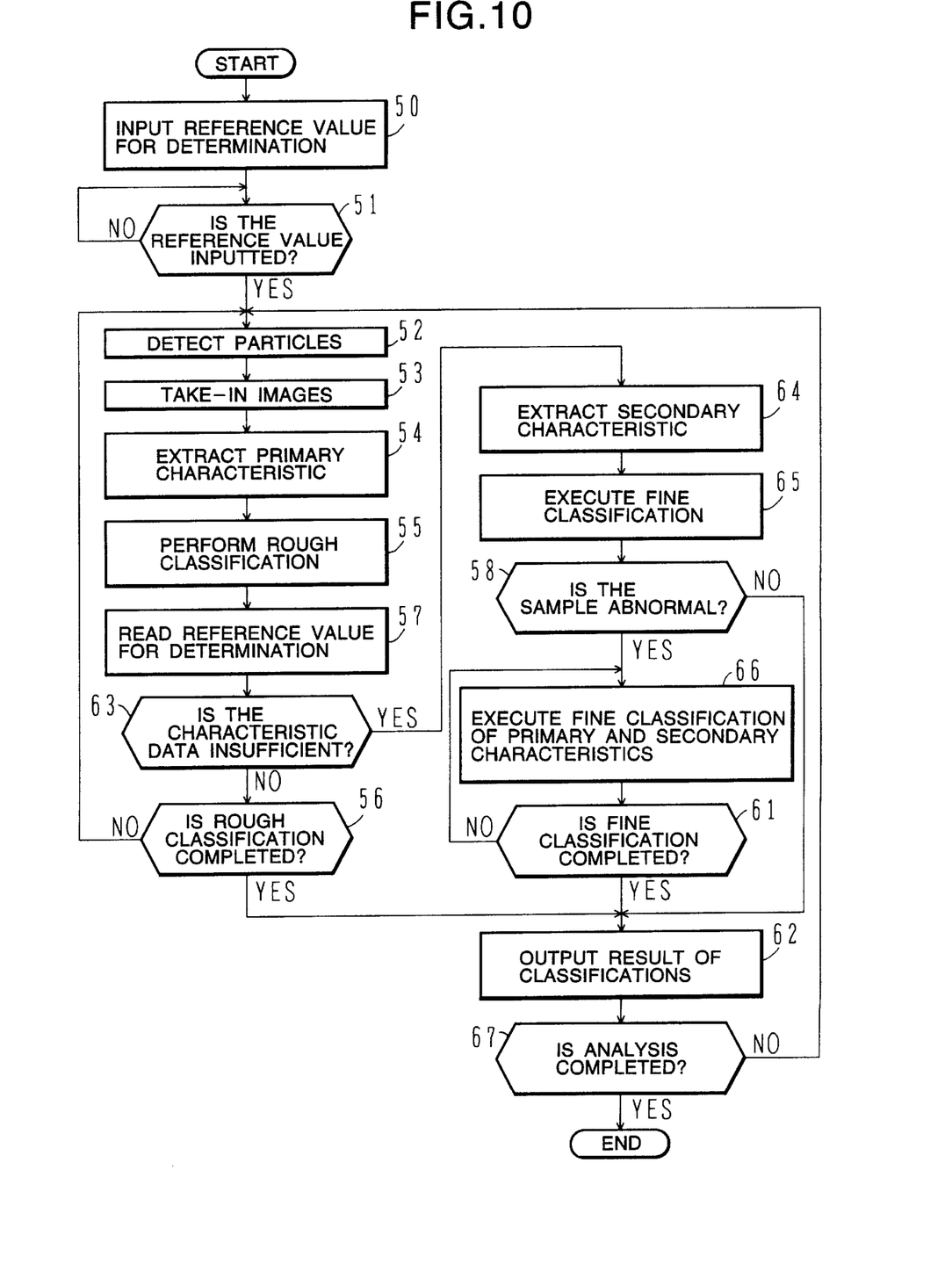
FIG. 10 is a flow chart showing the operation of the apparatus depicted in FIG. 9.

FIG. 9 is a schematic structural diagram of the flow type particle image analyzing apparatus according to a second embodiment of the present invention. FIG. 10 is a flow chart showing the operation of the apparatus depicted in FIG. 9. In FIGS. 9 and 10, parts equivalent to those in FIGS. 1 and 2 are identified by like numerals. In the embodiment shown in FIGS. 1 and 2, after rough classification of a desired number of samples is executed, a decision as to whether every sample is abnormal or not is made on the basis of a criterion for determination.

On the contrary, in the embodiment shown in FIGS. 9 and 10, reference values for determination are read in the middle of rough classification of samples, so that samples having a possibility of being abnormal are checked and subjected to more detailed fine classification than the rough classification to thereby determine whether every sample is abnormal or not. Then, the samples determined as being abnormal are subjected to fine classification.

In FIG. 9, a determination unit 301 has a rough classification determination unit 301*a* and a fine classification determination unit 301*b*. The structure of the embodiment in FIG. 9 as to other parts is the same as that of the embodiment in FIG. 1. Accordingly, a description of the other parts is omitted.

When reference values for determination are read in step 50 in FIG. 10 and then it is determined whether the inputting of the reference values is completed in step 51, particles are detected and images thereof are fetched in steps 52 and 53. Then, in step 54, primary characteristics for rough classification are extracted from the fetched particle images. In step 55, rough classification is executed by the rough classification unit 291.

Next, in step 57, the reference values stored in the reference value storage unit 300 are read by the rough classification determination unit 301*a*. Then, in step 63, the normality of the sample is determined on the basis of the reference values for determination. In the case where this determination cannot be made, that is, in the case where the sample has a possibility of being abnormal, characteristic data is added. When it is decided that the sample is not abnormal in the step 63, the process proceeds to step 56 in which a determination is made as to whether the rough classification is completed or not. When it is determined that the rough classification is not completed in the step 56, the process returns to the step 52. When it is determined that the rough classification is completed, the process proceeds to step 62.

In the step 62, results of the classification are outputted and then the process proceeds to step 67 in which a determination is made as to whether analysis is completed or not. When it is determined that the analysis is not completed in the step 67, the process returns to the step 52.

In the case where the sample has a possibility of being abnormal in the step 63, the process proceeds to step 64. In the step 64, the fine classification determination unit 301*b* makes the fine classification unit 290 extract secondary characteristic information (for example, increase of the number of samples, addition of color information, etc.), which comprises more detail than the primary characteristic extracted in the step 54. In step 65, the fine classification determination unit 301*b* makes the fine classification unit 290 execute fine classification. Then, the fine classification determination unit 301*b* fetches results of the fine classification executed by the fine classification unit 290 and, in step 58, makes a determination on the basis of the reference values stored in the reference value storage unit 300 as to whether the sample is abnormal or not. When it is determined that the sample is not abnormal in the step 58, the process proceeds to step 62.

When it is determined that the sample is abnormal in the step 58, the process proceeds to step 66 in which more detailed fine classification using the primary and secondary characteristics is executed by the fine classification unit 290. Then, in step 61, a determination is made as to whether the fine classification is completed or not. When it is determined that the fine classification is completed, results of the classification are outputted in the step 62. Then, in step 67, a determination is made as to whether analysis is completed or not. When it is determined that the analysis is not completed, the process returns to the step 52.

As described above, in the second embodiment of the present invention, when the result of the rough classification is inconclusive with respect to a particular sample, more detailed, fine classification is immediately executed to classify the particular sample. Further, a determination is made from results of the fine classification as to whether the sample is abnormal or not, so that the sample determined as being abnormal is finely classified more in detail. Accordingly, not only the same effect as in the embodiment of FIG. 1 can be obtained but also there arises an effect that abnormal samples can be detected at an early stage.

Moreover, in the second embodiment of the present invention, samples impossible of being determined by rough classification are picked out to be finely classified. Accordingly, the rough classification in the second embodiment can be made simpler than the rough classification in the embodiment of FIG. 1. Accordingly, the rough classification in the embodiment of FIG. 9 can be executed more speedily than the rough classification in the embodiment of FIG. 1.

Incidentally, also in the second embodiment, time zones free from analyzing operations are calculated automatically so that data transfer is executed in the spare time zones in the same manner as in the first embodiment of the present invention.

Although the aforementioned embodiments have shown the case where the present invention is applied to a flow type particle image analyzing apparatus, it is to be understood that the invention is not limited to the case of application to such a flow type particle image analyzing apparatus and that the invention may be applied to another apparatus as long as the apparatus serves to analyze images of a fluid sample such as urine, blood, or the like, containing particles.

What is claimed is:

1. A particle image analyzing apparatus, comprising:
   an image pick-up means for picking up images of particles contained in a fluid sample;
   an image memory for storing images of particles picked-up by said image pick-up means;
   an image analyzing unit for analyzing said images of said particles picked up by said image pick-up means;
   an input of a reference value, wherein said reference value represents a normal number of particles of a particular type for the fluid sample;
   a storer of said reference value given by said input, wherein the stored reference value is changeable by said input;
   a rough classification unit which uses a first set of parameters to identify and count the number of particles of the particular type contained in the fluid sample, wherein said rough classification unit determines whether the fluid sample is normal or abnormal by comparing the number of identified particles of the particular type with the stored reference value;
   a fine classification unit which analyzes particles contained in the sample with a second set of parameters, when said rough classification unit has determined the sample is abnormal, to determine a kind of abnormality, and
   a spare time determination unit which comprises:
      a memory storage unit which stores detected analysis start and end points of time, wherein said detected analysis start and end points of time define operating periods of time when said analyzing apparatus is operational, wherein said analysis start and end points of time are stored for each day over a predetermined number of days;
      a calculation unit which calculates a plurality of spare time zones from the defined operating periods, wherein each spare time zone of said plurality of spare time zones corresponds to a time of day in which the average of said operating periods of time when said analyzing apparatus is operational over the predetermined number of days is less than a predetermined level; and
      a transfer unit which transfers particle image data obtained by said image pick-up means to an external storage means during a spare time zone of the plurality of spare time zones.

2. A particle image analyzing apparatus according to claim 1,
   wherein said spare time determination unit selects a spare time zone from said plurality of spare time zones for transferring data with said transfer unit, and wherein if said image analyzing apparatus is operating during the selected spare time zone, said spare time determination unit selects another spare time zone for transferring particle image data.

3. A particle image analyzing apparatus, comprising:
   an image pick-up means for picking up images of particles contained in a fluid sample;
   an image memory for storing images of particles picked-up by said image pick-up means;
   an image analyzing unit for analyzing said images of said particles picked up by said image pick-up means;
   an input of a reference value, wherein said reference value represents a normal number of particles of a particular type for the fluid sample;
   a store of said reference value given by said input, wherein the stored reference value is changeable by said input;
   a rough classification unit which uses a primary characteristic of particles of a particular type to identify and count the number of particles of the particular type contained in the fluid sample, wherein said rough classification unit determines whether the fluid sample is normal or abnormal by comparing the number of identified particles of the particular type with the stored reference value, wherein the primary characteristic is determined from image parameters; and
   a fine classification unit which, when said rough classification unit cannot make a determination that said fluid sample is normal, uses a secondary characteristic of the particles of a particular type to identify and count the number of particles of the particular type contained in the fluid sample, wherein said fine classification unit determines the kind of abnormality by comparing the number of identified particles of the particular type with the stored reference value, wherein the secondary characteristic is determined from image parameters and the secondary characteristic is determined from more image parameter information than said primary characteristic; and
   a spare time determination unit which comprises:
      a memory storage unit which stores detected analysis start and end points of time, wherein said detected analysis start and end points of time define operating periods of time when said analyzing apparatus is operational, wherein said analysis start and end points of time are stored for each day over a predetermined number of days;

a calculation unit which calculates a plurality of spare time zones from the determined operating periods, wherein each spare time zone of said plurality of spare time zones corresponds to a time of day in which the average of said operating periods of time when said analyzing apparatus is operational over the predetermined number of days is less than a predetermined level; and a transfer unit which transfers particle image data obtained by said image pick-up means to an external storage means during a spare time zone of the plurality of spare time zones.

4. A particle image analyzing apparatus according to claim 3, wherein said spare time determination unit selects a spare time zone from said plurality of spare time zones for transferring data with said transfer unit, and wherein if said image analyzing apparatus is operating during the selected spare time zone, said spare time determination unit selects another spare time zone for transferring particle image data.

5. A particle image analyzing apparatus comprising:

an image pick-up means for picking up images of particles contained in a fluid sample;

an image memory for storing images of particles picked-up by said image pick-up means;

an image analyzing unit for analyzing said images of said particles picked up by said image pick-up means;

an input of a reference value, wherein said reference value represents a normal number of particles of a particular type for the fluid sample;

a storer of said reference value given by said input, wherein the stored reference value is changeable by said input;

a rough classification unit which uses at least one parameter selected from the group consisting of shape, color, and size to identify and count the number of particles of the particular type contained in the fluid sample, wherein said rough classification unit determines whether the fluid sample is normal or abnormal by comparing the number of identified particles of the particular type with the stored reference value;

a fine classification unit which analyzes particles contained in the sample with neural network identification theory, when said rough classification unit has determined the sample is abnormal, to determine a kind of abnormality; and a spare time determination unit which comprises:

a memory storage unit which stores detected analysis start and end points of time, wherein said detected analysis start and end points of time define operating periods of time when said analyzing apparatus is operational, wherein said analysis start and end points of time are stored for each day over a predetermined number of days;

a calculation unit which calculates a plurality of spare time zones from the defined operating periods, wherein each spare time zone of said plurality of spare time zones corresponds to a time of day in which the average of said operating periods of time when said analyzing apparatus is operational over the predetermined number of days is less than a predetermined level; and a transfer unit which transfers particle image data obtained by said image pick-up means to an external storage means during a spare time zone of the plurality of spare time zones.

\* \* \* \* \*